United States Patent [19]

Trod

[11] 3,951,608

[45] Apr. 20, 1976

[54] MIXING CUVETTE AND TIMING TURNTABLE FOR PROVIDING REACTION MIXTURES

[76] Inventor: Ernest Trod, 2376 Roosevelt Circle, Santa Clara, Calif. 95050

[22] Filed: Jan. 22, 1975

[21] Appl. No.: 542,963

[52] U.S. Cl. ............................ 23/259; 23/253 R
[51] Int. Cl.² ...................... G01N 1/14; G01N 1/18
[58] Field of Search ............ 23/259, 253, 230, 292; 356/246

[56] References Cited
UNITED STATES PATENTS

| | | | |
|---|---|---|---|
| 3,540,858 | 11/1970 | Rochte et al. | 23/253 X |
| 3,586,484 | 6/1971 | Anderson | 23/259 X |
| 3,681,029 | 8/1972 | Shapiro | 23/253 X |
| 3,773,423 | 11/1973 | Hach | 23/253 |
| 3,864,089 | 2/1975 | Tiffany et al. | 23/259 |
| 3,873,217 | 3/1975 | Anerson et al. | 23/259 |

*Primary Examiner*—R. E. Serwin
*Attorney, Agent, or Firm*—Flehr, Hohbach, Test, Albritton & Herbert

[57] ABSTRACT

A turntable is supported upon a support base and is urged rotationally through step increments at a constant stepped rate. The step rotation is accomplished by an air actuated ratchet mechanism. Peripheral depressions are provided for accepting a plurality of cuvettes for holding samples and reagents spaced apart within the cuvettes. A depending member on the cuvette is configured for contact by an air actuated extension arm for rocking the cuvette in its peripheral position on the turntable for mixing the sample and reagent. The extension arm is adjustable rotationally to contact the depending member on a cuvette at a predetermined rotational mix position on the turntable. A rotational reference position for the turntable is defined on the support. A predetermined time is thereby selected for reaction between the sample and the reagent dependent upon the selection of the mix position and the constant stepped rate of turn imparted to the turntable. In this fashion a mixed reactant solution is presented at the reference position which has undergone reaction for a predetermined period of time.

14 Claims, 8 Drawing Figures

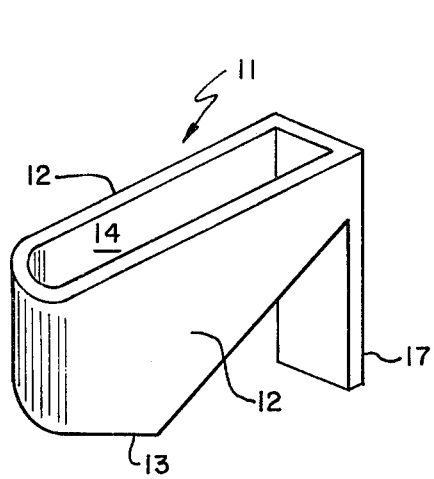
FIG.—1
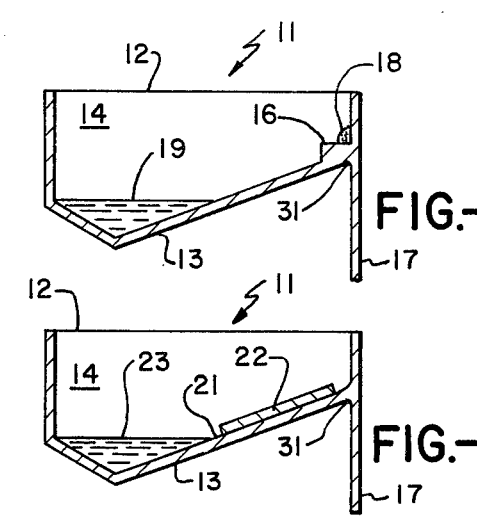
FIG.-2a
FIG.-2b
FIG.-2c
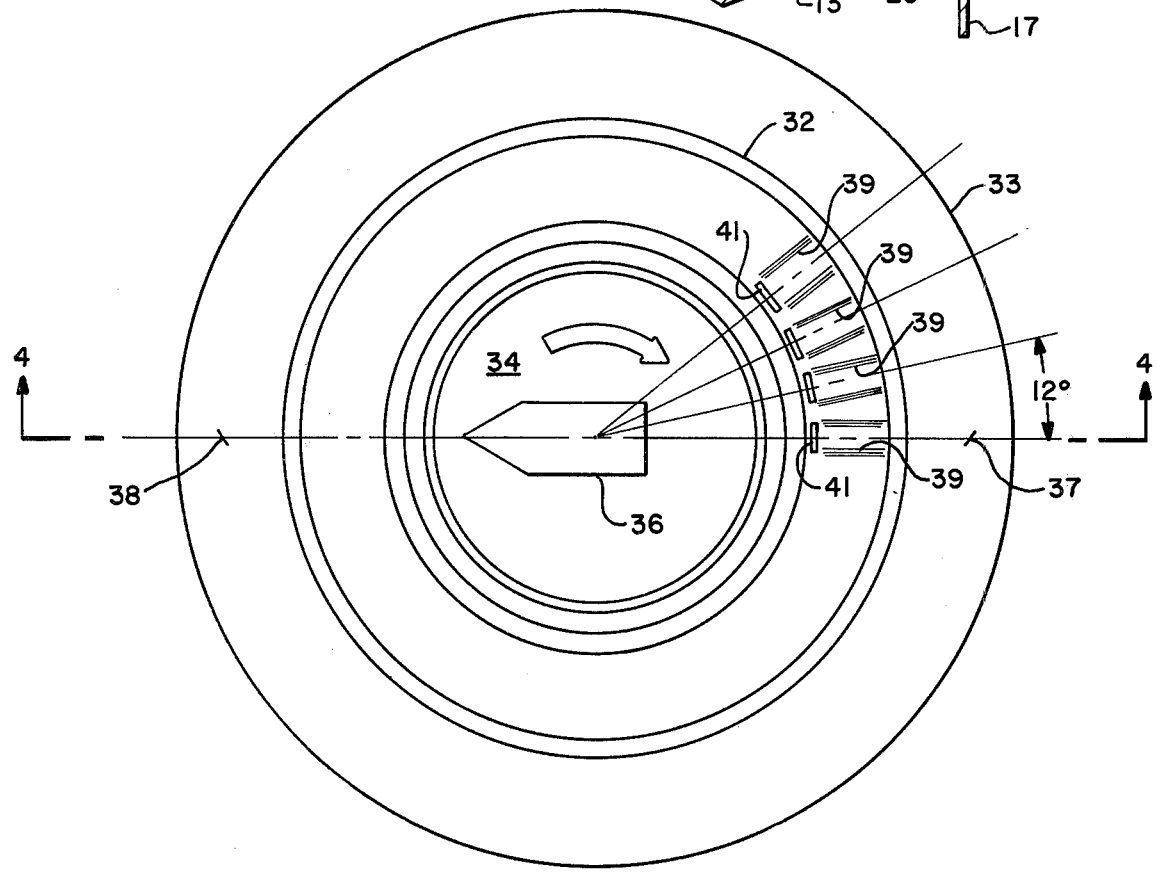
FIG.—3

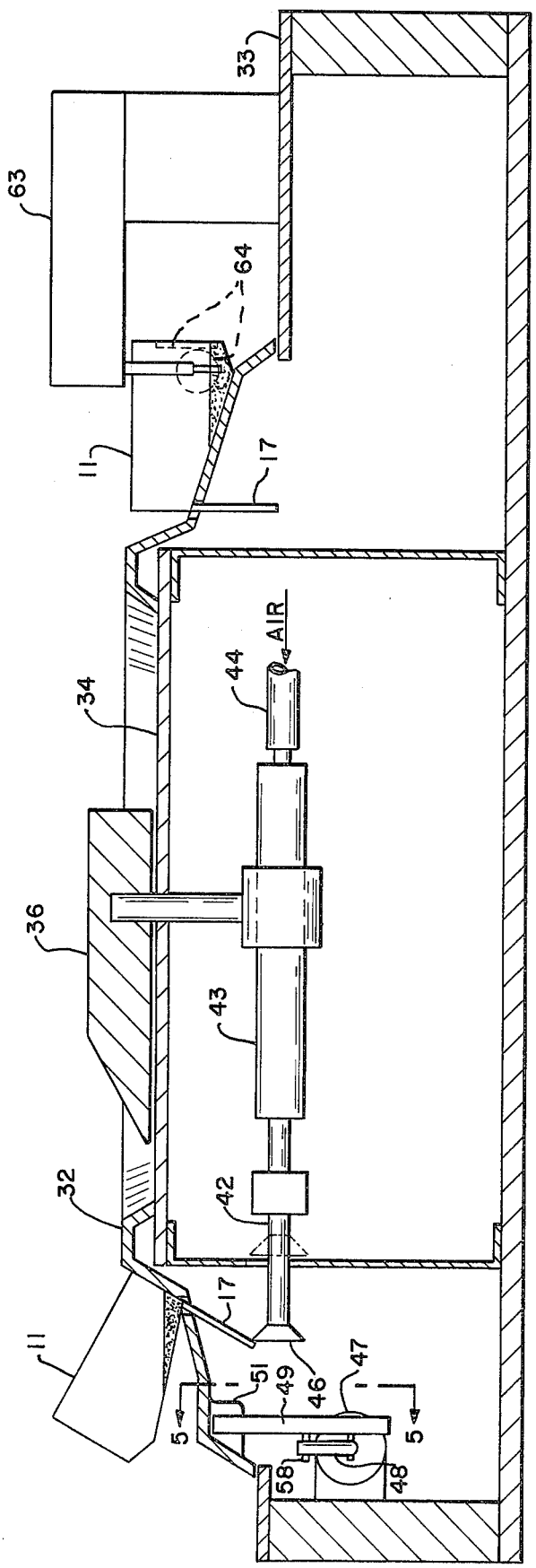
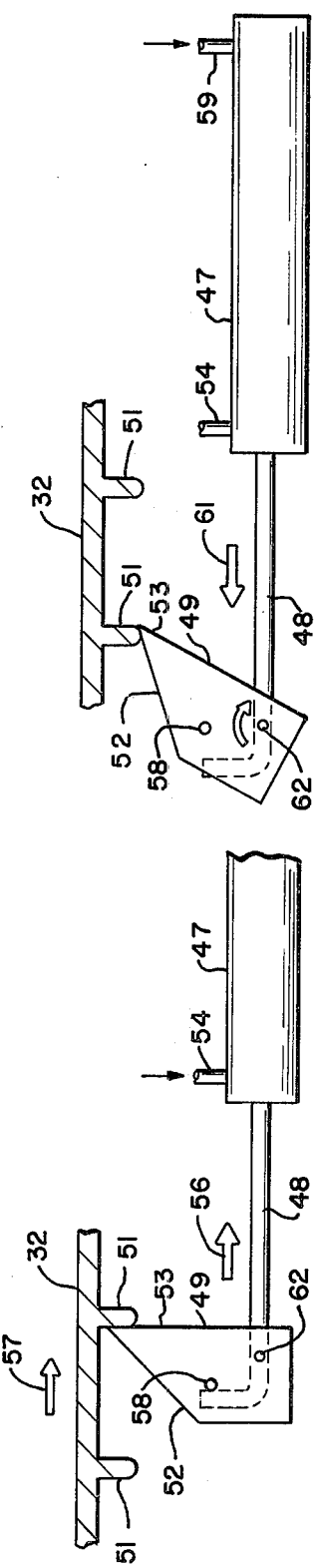
FIG.—4
FIG.—5
FIG.—6

MIXING CUVETTE AND TIMING TURNTABLE FOR PROVIDING REACTION MIXTURES

BACKGROUND OF THE INVENTION

This invention relates to an apparatus for providing reaction mixtures and more particularly to such apparatus for providing reaction mixtures which have interacted for a predetermined period of time.

Available automated reagent dispensing apparatus is generally expensive with accompanying limited flexibility since reagents available from the dispenser are limited due to a limited number of associated reservoirs. A great deal of mechanical intricacy is required for dispensing one reagent in one cuvette and another reagent in an adjacent cuvette, etc. A restricted number of reaction mixtures results.

Semi-automatic reaction mixture apparatus involves dispensing many different reagents in adjacent cuvettes. Subsequent dispensing of samples in the cuvettes provides reaction mixtures which may be timed and measured or observed at the end of predetermined reaction times. In this instance, time must be observed for a plurality of reactions occuring simultaneously and risk of incorrect sample-reagent mixtures is ever present.

There is therefore a need for a timed reaction mixture device in which accurate amounts of sample and reagent may be placed prior to mixing, and in which the reaction mixture may be automatically timed and presented to a measuring station.

SUMMARY AND OBJECTS OF THE INVENTION

Reaction mixtures are provided for obtaining characteristics from a sample. A rotating table has a predetermined rotational reference position and a predetermined rotational mixing position. A power source is provided for urging the rotating table between the mixing position and the reference position at a predetermined rate of rotation. A plurality of cuvettes are mounted peripherally on the rotating table for holding in spaced relation a sample and a reagent. The cuvette is disturbed at the mixing position so that the sample and reagent are mixed to form a reaction mixture. The reaction progresses as the table rotates to the reference position, whereupon the reaction mixture, having reacted for a predetermined period of time, is measured to determine the characteristics of the sample.

In general it is an object of the present invention to provide a mixing cuvette and timing turntable which provides accurate proportions of sample and reactant for reaction over a predetermined period of time.

Another object of the present invention is to provide a mixing cuvette and timing turntable in which sample and reagent may be predeposited prior to mixing.

Another object of the present invention is to provide a mixing cuvette and timing turntable which provides a reaction mixture facilitating a variety of measuring methods.

Another object of the present invention is to provide a mixing cuvette and timing turntable in which a large number of sample and reagent combinations may undergo reaction simultaneously.

Another object of the present invention is to provide a mixing cuvette and timing turntable of relatively simple construction for providing a large number of reaction mixtures in quick succession.

Additional objects and features of the invention will appear from the following description in which the preferred embodiment has been set forth in detail in conjunction with the accompanying drawings.

BRIEF DESCRIPTION OF THE DRAWINGS

FIG. 1 is an isometric view of a cuvette used in the disclosed invention.

FIG. 2A is a sectional view of one embodiment of the cuvette of FIG. 1.

FIG. 2B is a sectional view of another embodiment of the cuvette of FIG. 1.

FIG. 2C is a sectional view of an additional embodiment of the cuvette of FIG. 1.

FIG. 3 is a plan view of the timing turntable.

FIG. 4 is a sectional view along the line 4—4 of FIG. 3.

FIG. 5 is a sectional view along the line 5—5 of FIG. 4.

FIG. 6 is a partial sectional view of the ratchet mechanism of FIG. 5.

DESCRIPTION OF THE PREFERRED EMBODIMENT

A mixing cuvette 11 is shown in FIG. 1. Cuvette 11 has side and end walls 12 and a bottom wall 13. A reservoir 14 is defined by side walls 12 and bottom wall 13. Bottom wall 13 has a slope from one end of reservoir 14 to the other thereby providing a deep end and a shallow end in reservoir 14. A pedestal 16 is shown in FIG. 2A positioned in the shallow end, midway through the depth of reservoir 14. A depending member or lever 17 extends from one end of cuvette 11.

Various configurations of cuvette 11 are envisioned. FIG. 2A shows a configuration which may contain a sample 18 located on pedestal 16 and a reagent 19 located in reservoir 14. FIG. 2B has an internal planar surface 21 on bottom wall 13 for mounting a solid catalyst 22. A solution 23 for catalytic reaction is contained in reservoir 14. FIG. 2C shows a first reservoir 24 at the deep end within cuvette 11 and a second reservoir 26 at the shallow end within cuvette 11. A barrier 27 is positioned between reservoirs 24 and 26. Barrier 27 separates a substance 28 which may be deposited in reservoir 24 from a substance 29 which may be deposited in reservoir 26. As may be seen in each of FIGS. 2A through 2C, a force having a component applied substantially orthogonally against depending member 17 from right to left will tend to rotate cuvette 11 in a clockwise direction if cuvette 11 is restrained from lateral movement at the junction 31 of member 17 with bottom wall 13. In this fashion the reagent in the deep end of reservoir 14 will wash over the substance in the shallow end of the reservoir.

Turning to FIG. 3 a rotating table 32 is shown having a support base 33. Support base 33 has a central portion 34 upon which is mounted a rotatable selector 36 for selecting a predetermined mixing position rotationally relative to table 32. A rotational reference position 37 relative to table 32 is designated. As seen in FIG. 3 selector 36 indicates a selected mixing position 38 which may be 180° from reference position 37, for example. A plurality of depressions 39 exist on the periphery of rotating table 32 for receiving mixing cuvettes 11. A corresponding plurality of slots 41 are located adjacent each depression 39 for receiving depending members 17 when cuvette 11 is placed in depressions 39. It may be seen that in the described embodiments, depressions 39 are located approximately 12° apart.

Turning to FIG. 4 a plunger 42 is seen extending from cylinder 43. Plunger 42 is actuated by air directed into cylinder 43 through air inlet tube 44. An end 46 is formed on plunger 42 for contacting depending member 17 on cuvette 11.

A turntable drive cylinder 47 has extending therefrom a piston driven rod 48. Rod 48 has attached to the end thereof a ratchet member 49 for contacting teeth 51 on the underside of turntable 32.

Turning to FIG. 5 the manner in which turntable drive cylinder 47 urges turntable 32 rotationally at a cons.ant stepped rate may be seen. Ratchet member 49 has a cam surface 52 and a drive surface 53. When air pressure is directed to drive inlet tube 54 rod 48 is urged in the direction of arrow 56 engaging drive surface 53 with teeth 51 and stepping turntable 32 in the direction of arrow 57. Pin 58 prevents rotation of ratchet member 49 when urged in the direction of arrow 56.

When pressure is directed to a return air inlet 59, piston driven rod 48 is urged in the direction of arrow 61 in FIG. 6, whereby cam surface 52 contacts one of the teeth 51 and ratchet member 49 rotates about a pin 62 allowing ratchet member 49 to clear teeth 51 without rotating turntable 32. Rod 48 is thereby positioned in its extended position, preparatory to being subsequently driven in the direction of arrow 56 by application of pressure to drive air inlet 54 as described above. In this fashion, turntable 32 is driven rotationally in a stepped manner. The stepped rotational movement of turntable 32 may be a periodic stepped rotation, providing a constant rotational rate for turntable 32 over a number of periods.

Returning to FIG. 4 the operation of the mixing will be described. Plunger 42 is urged toward an extended position by application of air pressure through air inlet tube 44. Upon the application of such pressure through tube 44 end 46 on plunger 42 contacts depending member 17 causing cuvette 11 to rock in a clockwise direction and the reagent 19 overflows sample 18 on pedestal 16 in FIG. 2A, for example. Reagent 19 and sample 18 are washed together into the bottom of reservoir 14 when plunger 42 is retracted upon the removal of pressure from air inlet tube 44. Turntable 32 is thereafter stepped rotationally from mixing position 38 to reference position 37. Upon arrival of cuvette 11 at reference position 37 a measurement may be taken. The reaction mixture has undergone reaction for the time it takes the table to rotate from the mixing position 38 to reference position 39.

Any one of a number of measuring means is envisioned including aspiration by aspirator 63 located at reference position 37. In the event the reaction mixture is aspirated measurement may subsequently be made by spectrophotometer, fluorometer, nephelometer, or radioactive counter for example. In the absence of aspirator 63, optical measurements may be made of the reaction solution in place in the cuvette 11. Optical areas 64 on cuvette 11 may be configured to allow passage of light energies through side walls 12 for determining particular characteristics of the reaction solution. In the latter case, associated light sources and receivers would be implemented for measurement of reaction solution characteristics.

Certain separation techniques, such as ion exchange or catalytic absorption, may be undertaken when cuvette 11 reaches reference position 37 containing a reaction mixture therein.

A cuvette has been disclosed in which may be deposited, in spaced relation, a sample and a reagent. The cuvette is configured to be mounted on the periphery of a rotating table, to be disturbed thereon for mixing the sample and the reagent together. Subsequent predetermined periodic step rotation of the table provides for a predetermined amount of time from the rotational position of mixing to the rotational reference position. The features of the invention include the ability to keep the components separated within the cuvette until the cuvette reaches the predetermined rotational mixing position, and provision for a predetermined reaction time from the mixing position to the reference position.

I claim:

1. An apparatus for providing reaction mixtures for displaying characteristics of a sample comprising a support base, a rotating table mounted for rotational movement relative to said support base, said support base having thereon a predetermined rotational reference position, means mounted on said support base for defining thereon a predetermined rotational mixing position, said mixing position being located at a predetermined angle relative to said reference position, means for urging said rotational table through said predetermined angle from said mixing position to said reference position at a predetermined rate, a cuvette mounted on said rotating table for holding the sample and a reagent in spaced relation therein, means mounted on said support base for disturbing said cuvette at said mixing position only for intermixing said sample and reagent to form the reaction mixture, whereby a reaction progresses for the period of time said rotating table takes to rotate at said predetermined rate through said predetermined angle.

2. An apparatus for providing reaction mixtures as in claim 1 wherein said means for defining said mixing position comprises a rotatable selector for setting said predetermined angle, whereby the reaction time of the reaction solution may be selected.

3. An apparatus for providing reaction mixtures as in claim 1 wherein said cuvette comprises a container, an interior pedestal in said container for holding said sample, a reservoir in said container adjacent to said pedestal for holding said reagent, and an external member on said container for contact with said means for disturbing so that said cuvette is rocked into a position at said mixing position such that said reagent overruns said sample.

4. An apparatus for providing reaction mixtures as in claim 1 wherein said cuvette comprises a container, a surface on the interior of said container for positioning a catalyst thereon, a reservoir in said container for containing a solution for catalytic reaction, and an external member on said container for contact with said means for disturbing so that said cuvette is rocked into a position such that said solution overruns said catalyst.

5. An apparatus for providing reaction mixtures as in claim 1 wherein said cuvette comprises a container, a first reservoir in said container for containing one substance to be mixed, a second reservoir in said container for containing a second substance to be mixed, a barrier disposed between said first and second reservoirs, and an external member on said container for contact with said means for disturbing so that said cuvette is rocked into a position such that said barrier is overrun by said one substance and the reaction mixture is thereafter substantially contained in said second reservoir.

6. An apparatus for providing timed reaction mixtures comprising a turntable, said means for supporting having a rotational reference position and a rotational mixing position thereon with a predetermined angle therebetween, means for supporting said turntable for rotation thereon, means for driving said turntable rotationally at a predetermined rate mounted on said means for supporting, a cuvette mounted on said turntable for holding substances to be mixed therein in a spaced relation in a first orientation and for mixing the substances in a second orientation, means mounted on said means for supporting for urging said cuvette to assume said second orientation at said rotational mixing posotion, whereby the substances undergo mix reactions for a time period determined by said predetermined angle and said predetermined rotational rate.

7. An apparatus as in claim 6 together with means for selecting angular location of said rotational mixing position whereby the mix reaction time period may be selected.

8. An apparatus as in claim 6 wherein said cuvette comprises a container, an interior pedestal in said container for holding said sample, a reservoir in said container adjacent to said pedestal for holding said reagent, and an external member on said container for contact with said means for disturbing so that said cuvette is rocked into said second orientation at said mixing position such that said reagent overruns said sample.

9. An apparatus as in claim 6 wherein said cuvette comprises a container, a surface on the interior of said container for positioning a catalyst thereon, a reservoir in said container for containing a solution for catalytic reaction, and an external member on said container for contact with said means for disturbing so that said cuvette is rocked into said second orientation such that said solution overruns said catalyst.

10. An apparatus as in claim 6 wherein said cuvette comprises a container, a first reservoir in said container for containing one substance to be mixed, a second reservoir in said container for containing a second substance to be mixed, a barrier disposed between said first and second reservoirs, and an external member on said container for contact with said means for disturbing so that said cuvette is rocked into said second orientation such that said barrier is overrun by said one substance and the reaction mixture is thereafter substantially contained in said second reservoir.

11. A mixing cuvette adapted to be supported by an underlying surface having an aperture therethrough, comprising a plurality of walls defining a reservoir having one open end, said plurality of walls including a bottom wall having a slope thereto whereby said reservoir has a deep end and a shallow end, means formed in said shallow end for holding a substance to be mixed in isolation from said deep end, and a depending lever formed as an extension of one of said plurality of walls and adapted to extend through the aperture in the underlying surface, so that when a force is applied substantially orthogonally to said depending lever, said reservoir is rotated on the underlying surface, whereby a reagent deposited in said deep end overruns and intermixes with said substance in said shallow end.

12. A mixing cuvette as in claim 11 wherein said means for holding comprises a pedestal for placement of said substance thereupon.

13. A mixing cuvette as in claim 11 wherein said means for holding comprises a planar surface.

14. A mixing cuvette as in claim 11 wherein said means for holding comprises a barrier located between said deep and shallow ends.

* * * * *